United States Patent
Shibaz et al.

(10) Patent No.: US 11,819,568 B2
(45) Date of Patent: *Nov. 21, 2023

(54) DOSAGE FORM FOR VAPORIZATION AND SMOKING

(71) Applicant: TRICHOMESHELL LTD., Givat Chen (IL)

(72) Inventors: Guy Shibaz, Kibbutz Ruchama (IL); Dror Shalitin, Raanana (IL); Gilad Asher Livni, Tsafaria (IL); Shay Avraham Sarid, Raanana (IL)

(73) Assignee: TRICHOMESHELL LTD., Givat Chen (IL)

( * ) Notice: Subject to any disclaimer, the term of this patent is extended or adjusted under 35 U.S.C. 154(b) by 281 days.

This patent is subject to a terminal disclaimer.

(21) Appl. No.: 17/400,359

(22) Filed: Aug. 12, 2021

(65) Prior Publication Data

US 2021/0369603 A1    Dec. 2, 2021

Related U.S. Application Data

(63) Continuation of application No. 16/307,611, filed as application No. PCT/IL2017/050718 on Jun. 28, 2017, now Pat. No. 11,701,323.

(60) Provisional application No. 62/355,336, filed on Jun. 28, 2016.

(51) Int. Cl.

| A61K 9/00 | (2006.01) |
| A61K 31/352 | (2006.01) |
| A61M 15/00 | (2006.01) |
| A61K 45/06 | (2006.01) |
| A61K 31/05 | (2006.01) |
| A61M 11/04 | (2006.01) |
| A61K 9/06 | (2006.01) |
| A61K 36/185 | (2006.01) |
| A61K 47/10 | (2017.01) |
| A61K 47/36 | (2006.01) |

(52) U.S. Cl.
CPC ............... *A61K 9/007* (2013.01); *A61K 9/06* (2013.01); *A61K 31/05* (2013.01); *A61K 31/352* (2013.01); *A61K 36/185* (2013.01); *A61K 45/06* (2013.01); *A61K 47/10* (2013.01); *A61K 47/36* (2013.01); *A61M 11/04* (2013.01); *A61M 15/00* (2013.01)

(58) Field of Classification Search
None
See application file for complete search history.

(56) References Cited

U.S. PATENT DOCUMENTS

| 6,713,048 | B2 | 3/2004 | Peart et al. |
| 8,629,177 | B2 | 1/2014 | Castor et al. |
| 8,735,374 | B2 | 5/2014 | Zerbe et al. |
| 9,023,322 | B2 | 5/2015 | Van Damme et al. |
| 2003/0229027 | A1 | 12/2003 | Eissens et al. |
| 2004/0022755 | A1 | 2/2004 | Kamath |
| 2005/0042172 | A1 | 2/2005 | Whittle |
| 2005/0063686 | A1 | 3/2005 | Whittle et al. |
| 2007/0072939 | A1 | 3/2007 | Kupper |
| 2008/0000488 | A1 | 1/2008 | Nadimi et al. |
| 2008/0081834 | A1 | 4/2008 | Lippa et al. |
| 2012/0160253 | A1 | 6/2012 | Coleman et al. |
| 2014/0271940 | A1 | 9/2014 | Wurzer |
| 2015/0136158 | A1 | 5/2015 | Stevens et al. |
| 2015/0181925 | A1 | 7/2015 | Turner |
| 2016/0157521 | A1 | 6/2016 | Woodcock et al. |
| 2016/0183589 | A1 | 6/2016 | Born et al. |
| 2017/0202895 | A1 | 8/2017 | Hugh |

FOREIGN PATENT DOCUMENTS

| CA | 2749933 A1 | 8/2010 |
| WO | 2005044093 A2 | 5/2005 |
| WO | 2011063164 A2 | 5/2011 |
| WO | 2012075473 A1 | 6/2012 |
| WO | 2013019271 A1 | 2/2013 |
| WO | 2013165251 A1 | 11/2013 |
| WO | 2016001924 A2 | 1/2016 |
| WO | 2016019353 A1 | 2/2016 |
| WO | 2016022936 A1 | 2/2016 |
| WO | 2016092539 A1 | 6/2016 |
| WO | 2016181394 A1 | 11/2016 |
| WO | 2017218845 A1 | 12/2017 |

OTHER PUBLICATIONS

Xiao, et al., Biodegradable Thermoresponsive Hydrogels for Aqueous Encapsulation and Controlled Release of Hydrophilic Model Drugs, Biomacromolecules, Jul.-Aug. 2005, vol. 6, No. 4, pp. 2131-2139; Retrieved Oct. 13, 2021; https://doi.org/10.1021/bm050116t.

Solowij, et al., A protocol for the delivery of cannabidiol (CBD) and combined CBD and 9-tetrahydrocannabinol (THC) by vaporization, BMC Pharmacology and Toxicology, Oct. 16, 2014, vol. 15, No. 58, pp. 1-8; Retrieved Oct. 13, 2021 from: http://www.biomedcentral.com/2050-6511/15/58.

CannabisCapsules.com "About Us"; Downloaded on Feb. 28, 2019 from: http://www.cannabiscapsules.com/about-us; Retrieved Oct. 13, 2021.

Marinol.com; Downloaded on Feb. 28, 2019 from: http://www.marinol.com/; Retrieved Oct. 13, 2021.

PCT International Search Report for International Application No. PCT/IL2017/050718, dated Sep. 11, 2017, 5pp.

PCT Written Opinion of the International Searching Authority for International Application No. PCT/IL2017/050718, dated Sep. 11, 2017, 6pp.

*Primary Examiner* — Bong-Sook Baek

(74) *Attorney, Agent, or Firm* — The Roy Gross Law Firm, LLC; Roy Gross

(57) ABSTRACT

Embodiments of the disclosure relate to dosage forms intended for smoking, vaporization and/or inhalation and to methods for the preparations thereof.

9 Claims, 4 Drawing Sheets

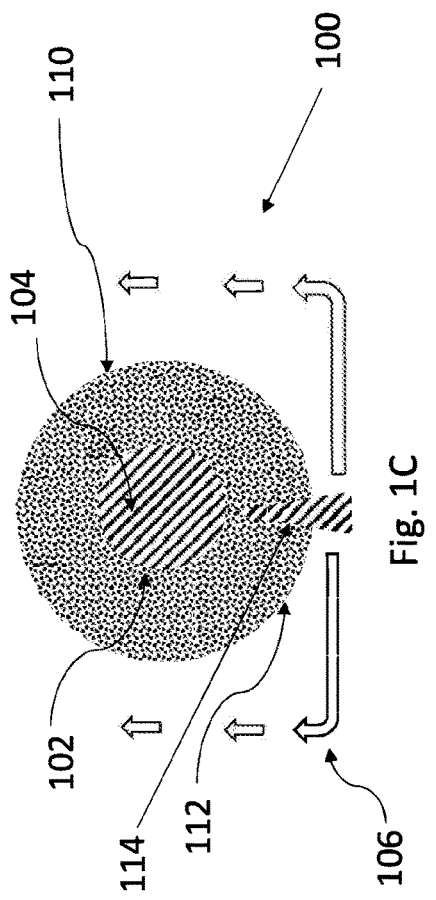
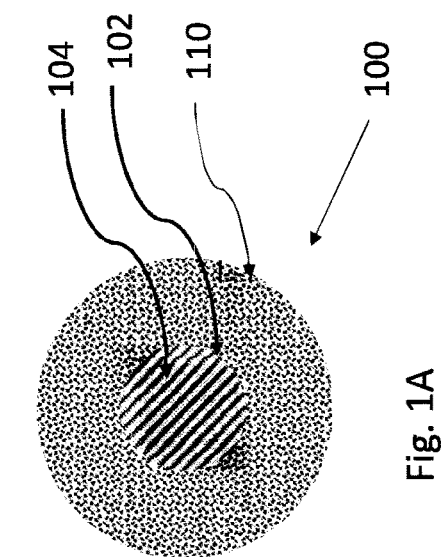
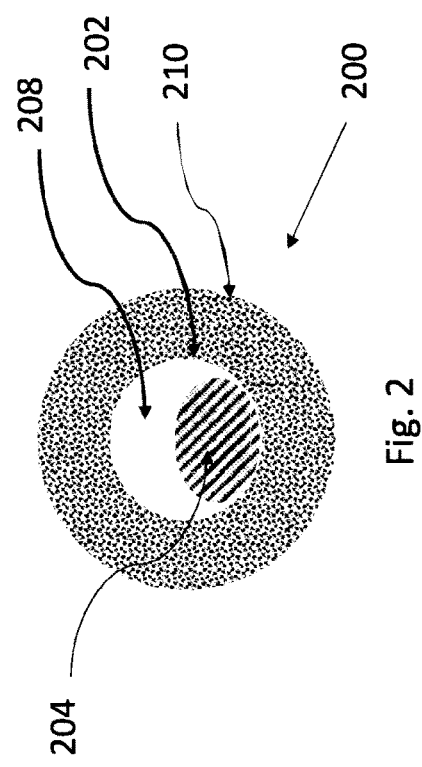
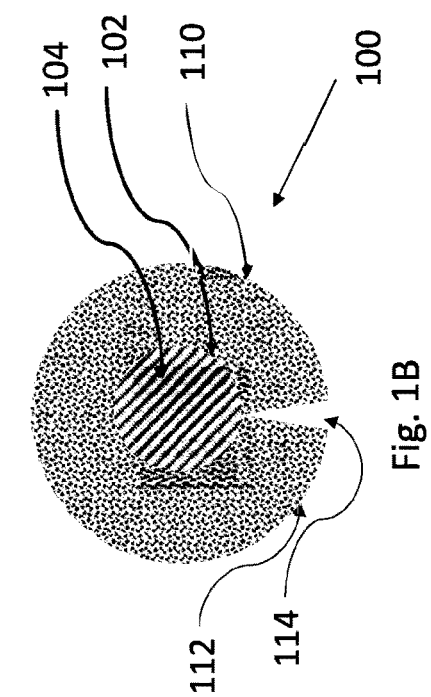

DOSAGE FORM FOR VAPORIZATION AND SMOKING

RELATED APPLICATIONS

This application is a continuation of U.S. application Ser. No. 16/307,611 filed on Dec. 6, 2018, which is a National Phase of PCT Patent Application No. PCT/IL2017/050718 having International filing date of Jun. 28, 2017, which claims the benefit of priority of U.S. Provisional Application No. 62/355,336 filed on Jun. 28, 2016. The contents of the above applications are all incorporated by reference as if fully set forth herein in their entirety.

FIELD

Embodiments of the disclosure relate to dosage forms intended for smoking, vaporization and/or inhalation and to methods for the preparations thereof.

BACKGROUND

For many years cannabis has been used as a medicament for use in the treatment of various diseases and disorders. The interest in the pharmacology of cannabis goes back hundreds of years. In addition to uses as anaesthetics, spasmolytics and hypnotics, cannabinoids have been used to combat emesis and nausea induced by cancer chemotherapy, and also in the treatment of glaucoma.

Cannabinoids, which are substituted meroterpenes, are the major active constituents of cannabis. The most important natural cannabinoid is the psychoactive tetrahydrocannabinol ((−)-trans-$\Delta^9$-tetrahydrocannabinol; THC); others include the non-psychoactive (but pharmaceutically active) compounds cannabidiol (CBD) and cannabigerol (CBG). Cannabinoids can be administered by a variety of routes. Because of their high lipid solubility, topical administration is possible in locations such as, for example, the eye or the nose. However, this has been of very limited applicability.

Smoking has been the most commonly used method of administration of cannabis, typically using crude marijuana, which includes cannabinoids. Much of the total THC in crude cannabis is not free THC but tetrahydrocannabinolic acid. The heat of combustion formed in the smoking device (e.g. a cigarette, a vaporizer or a waterpipe), upon advancing towards the vicinity of the cannabis, converts the THC acid to free THC through decarboxylation. Thereafter, the heat volatizes the THC so that it can be inhaled with the smoke into the lungs. The high lipid-solubility of THC allows it to cross the alveolar membrane rapidly, entering the blood in the pulmonary capillaries, and allowing a fast uptake into the brain.

U.S. Pat. No. 6,713,048 discloses a method of administering a THC to a patient, which comprises the steps of providing a solution comprising a pharmaceutically acceptable form of THC in a hydrofluoroalkane; aerosolizing the THC solution to provide respirable droplets comprising THC; and administering a pharmaceutically effective dose of said respirable droplets to a patient's lungs.

WO 2013/165251 discloses a method for preparing a THC isolate from a crude solvent extract of cannabis plant material. The method comprises providing a crude solvent extract of cannabis plant material containing, by weight of dry matter, 20-90% THC, 0.1-2.0% Cannabinol (CBN) and 0.1-1.0% Cannabidiol (CBD); subjecting the crude extract to thin film evaporation to obtain a refined extract; chromatographically fractionating the refined extract to produce one or more high purity fractions having a THC content higher than a preset value and one or more low purity fractions having a THC content lower than said preset value, wherein the preset value is in the range of 95-99% by weight of dry matter; subjecting the one or more high purity fractions to another thin film evaporation; and collecting a THC isolate containing at least 97% THC by weight of dry matter.

WO 2016/019353 discloses a pharmaceutical formulation of cannabis compounds, which is suitable for pulmonary delivery. The formulation comprises a volatile liquid, which includes a mixture of: a cannabis oil extract, and an aerosol precursor. The medicinal cannabis compound may include cannabinoids, terpenes, flavonoids, phytosterols, and/or other medicinally relevant compounds found in cannabis. WO 2016019353 also discloses an apparatus for converting the volatile liquid into particles suitable for pulmonary delivery.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods, which are meant to be exemplary and illustrative, not limiting in scope.

In some embodiments, there is provided a temperature dependent release dosage form for smoking, vaporization and/or inhalation, the dosage form comprising an active material comprising at least one cannabis ingredient; and a polymeric wall encapsulating said active material, said polymeric wall comprises a gellable polyol, wherein said wall is configured to prevent passage of said active material therethrough at temperatures lower than 45° C.

In some embodiments, there is provided a temperature dependent release dosage form for smoking, vaporization and/or inhalation, the dosage form comprising an active material comprising at least one cannabis ingredient; and a polymeric wall encapsulating said active material, said polymeric wall comprises a gellable polyol, wherein said wall is configured to allow passage of said active material therethrough at temperatures higher than 80° C.

In some embodiments, there is provided a temperature dependent release dosage form for smoking, vaporization and/or inhalation, the dosage form comprising an active material comprising at least one cannabis ingredient; and a polymeric wall encapsulating said active material, said polymeric wall comprises a gellable polyol, wherein said wall is configured to allow passage of said active material therethrough at temperatures higher than 80° C., and prevent passage of said active material therethrough at temperatures lower than 45° C.

In some embodiments, there is provided a temperature dependent release dosage form for smoking, vaporization and/or inhalation, the dosage form comprising an active material comprising at least one terpene compound; and a polymeric wall encapsulating said active material, said polymeric wall comprises a gellable polyol, wherein said wall is configured to prevent passage of said active material therethrough at temperatures lower than 45° C.

In some embodiments, there is provided a temperature dependent release dosage form for smoking, vaporization and/or inhalation, the dosage form comprising an active material comprising at least one terpene compound; and a polymeric wall encapsulating said active material, said polymeric wall comprises a gellable polyol, wherein said wall is configured to allow passage of said active material therethrough at temperatures higher than 80° C.

In some embodiments, the active material includes raw cannabis, cannabis extract and/or cannabis oil. In some embodiments, the active material consists of raw cannabis, cannabis extract and/or cannabis oil. In some embodiments, the active material includes raw cannabis. In some embodiments, the active material consists of raw cannabis. In some embodiments, the active material includes cannabis oil. In some embodiments, the active material consists of cannabis oil. In some embodiments, the active material includes cannabis extract. In some embodiments, the active material consists of cannabis extract.

In some embodiments, the active material includes a mixture of at least one cannabis ingredient and an additive. In some embodiments, the active material includes a mixture of cannabis and an additive. In some embodiments, the active material includes a mixture of cannabis oil and an additive. In some embodiments, the active material includes a mixture of cannabis extract and an additive. In some embodiments, the additive includes a gellable polysaccharide. In some embodiments, the additive includes a gellable polysaccharide and/or at least one terpene compound. In some embodiments, the additive includes a gellable polyol. In some embodiments, the additive includes at least one terpene compound. In some embodiments, the additive includes a gellable polysaccharide and at least one terpene compound. In some embodiments, the active material includes a mixture of cannabis oil and at least one terpene compound. In some embodiments, the active material consists of a mixture of cannabis oil and at least one terpene compound.

In some embodiments, the polymeric wall is a non-stick polymeric wall. In some embodiments, the dosage form is non-sticky.

In some embodiments, the polymeric wall further includes a second polyol. In some embodiments, the second polyol is a liquid at room temperature. In some embodiments, the second polyol includes glycerin. In some embodiments, the polymeric wall includes a mixture of a gellable polyol and a second polyol. In some embodiments, the polymeric wall consists of a mixture of a gellable polyol and a second polyol.

In some embodiments, the gellable polyol includes a gellable polysaccharide. In some embodiments, the gellable polyol is a gellable polysaccharide.

In some embodiments, the gellable polysaccharide includes a heteropolysaccharide, a polycarbohydrate, agarose, agar, agar-agar, cellulose, hydroxypropyl-cellulose, methylcellulose, hydroxypropylmethyl-cellulose, gelrite, phytagel, xanthan, xylinan, gellan, curdlan, pullulan, dextran, scleroglucan, schizophyllan, alginic acid, sodium alginate, or a combination thereof. In some embodiments, the gettable polysaccharide is selected from a heteropolysaccharide, a polycarbohydrate, agarose, agar, agar-agar, cellulose, hydroxypropyl-cellulose, methylcellulose, hydroxypropylmethyl-cellulose, gelrite, phytagel, xanthan, xylinan, gellan, curdlan, pullulan, dextran, scleroglucan, schizophyllan, alginic acid, sodium alginate, or a combination thereof.

In some embodiments, the polymeric wall has a stiffness within a specific range. In some embodiments, the polymeric wall has a stiffness within a specific range, such that the dosage form is resistant to breaking upon application of external force by a user's fingers. In some embodiments, the polymeric wall has a stiffness within a specific range, such that the dosage form is resistant to breaking upon application of external force of 250 N.

In some embodiments, the polymeric wall has a hardness within a specific range. In some embodiments, the polymeric wall has a hardness within a specific range, such that the dosage form is resistant to breaking upon application of external force by a user's fingers. In some embodiments, the polymeric wall has a hardness within a specific range, such that the dosage form is resistant to breaking upon application of external force of 250 N.

In some embodiments, the polymeric wall has a rigidity within a specific range. In some embodiments, the polymeric wall has a rigidity within a specific range, such that the dosage form is resistant to breaking upon application of external force by a user's fingers. In some embodiments, the polymeric wall has a rigidity within a specific range, such that the dosage form is resistant to breaking upon application of external force of 250 N.

In some embodiments, the polymeric wall includes no more than about 20% water. In some embodiments, the polymeric wall includes no more than about 15% water. In some embodiments, the polymeric wall includes no more than about 10% water. In some embodiments, the polymeric wall includes no more than about 5% water. In some embodiments, the polymeric wall includes no more than about 4% water. In some embodiments, the polymeric wall includes no more than about 3% water. In some embodiments, the polymeric wall includes no more than about 2% water. In some embodiments, the polymeric wall includes no more than about 1% water.

In some embodiments, the polymeric wall is configured to prevent passage of said active material therethrough at temperatures lower than 50° C. In some embodiments, the polymeric wall is configured to prevent passage of said active material therethrough at temperatures lower than 60° C. In some embodiments, the polymeric wall is configured to prevent passage of said active material therethrough at temperatures lower than 70° C. In some embodiments, the polymeric wall is configured to prevent passage of said active material therethrough at temperatures lower than 80° C. In some embodiments, the polymeric wall is configured to prevent passage of said active material therethrough at temperatures lower than 90° C.

In some embodiments, the gellable polyol does not melt at temperatures lower than 45° C. In some embodiments, the gellable polyol does not melt at temperatures lower than 50° C. In some embodiments, the gellable polyol does not melt at temperatures lower than 60° C. In some embodiments, the gellable polyol does not melt at temperatures lower than 70° C.

In some embodiments, the polymeric wall does not exhibit hysteresis at temperatures lower than 45° C. In some embodiments, the polymeric wall does not exhibit hysteresis at temperatures lower than 50° C. In some embodiments, the polymeric wall does not exhibit hysteresis at temperatures lower than 60° C. In some embodiments, the polymeric wall does not exhibit hysteresis at temperatures lower than 70° C.

In some embodiments, the gellable polyol does not substantially dissolve in water at temperatures lower than 45° C. In some embodiments, the gellable polyol does not substantially dissolve in water at temperatures lower than 50° C. In some embodiments, the gellable polyol does not substantially dissolve in water at temperatures lower than 60° C. In some embodiments, the gellable polyol does not substantially dissolve in water at temperatures lower than 70° C.

In some embodiments, the polymeric wall is configured to allow passage of said active material therethrough at temperatures higher than 140° C. In some embodiments, the polymeric wall is configured to allow passage of said active material therethrough at temperatures higher than 120° C. In some embodiments, the polymeric wall is configured to allow passage of said active material therethrough at temperatures higher than 100° C. In some embodiments, the polymeric wall is configured to allow passage of said active material therethrough at temperatures higher than 80° C. In some embodiments, the polymeric wall is configured to allow passage of said active material therethrough at temperatures higher than 70° C. In some embodiments, the polymeric wall is configured to allow passage of said active material therethrough at temperatures higher than 60° C.

In some embodiments, the gellable polyol melts at temperatures higher than 140° C. In some embodiments, the gellable polyol melts at temperatures higher than 120° C. In some embodiments, the gellable polyol melts at temperatures higher than 100° C. In some embodiments, the gellable polyol melts at temperatures higher than 90° C. In some embodiments, the gellable polyol melts at temperatures higher than 80° C.

In some embodiments, the gellable polyol is combustible. In some embodiments, the gellable polysaccharide is combustible. In some embodiments, the polymeric wall is combustible.

In some embodiments, the polymeric wall further includes a combustion promoter. In some embodiments, the combustion promoter includes a hydrocarbon.

In some embodiments, the polymeric wall exhibits hysteresis at temperatures higher than 140° C. In some embodiments, the polymeric wall exhibits hysteresis at temperatures higher than 120° C. In some embodiments, the polymeric wall exhibits hysteresis at temperatures higher than 100° C. In some embodiments, the polymeric wall exhibits hysteresis at temperatures higher than 80° C. In some embodiments, the polymeric wall exhibits hysteresis at temperatures higher than 70° C.

In some embodiments, the active material includes more carboxylic moieties than decarboxylated moieties. In some embodiments, the active material includes less than 20% decarboxylated moieties based on the total number of carboxylic moieties in the active material. In some embodiments, the active material includes less than 10% decarboxylated moieties based on the total number of carboxylic moieties in the active material. In some embodiments, the active material includes less than 5% decarboxylated moieties based on the total number of carboxylic moieties in the active material. In some embodiments, the active material includes less than 2% decarboxylated moieties based on the total number of carboxylic moieties in the active material. In some embodiments, the active material includes less than 1% decarboxylated moieties based on the total number of carboxylic moieties in the active material. In some embodiments, the active material includes essentially no decarboxylated moieties. In some embodiments, the carboxylic moieties undergo decarboxylation at temperatures higher than 100° C.

In some embodiments, the dosage form further includes a weight. In some embodiments, the polymeric wall encapsules said weight.

In some embodiments, the weight surrounds said polymeric wall. In some embodiments, the weight is perforated.

In some embodiments, the weight includes a noncombustible material. In some embodiments, the noncombustible material includes a metal, glass, silica, clay or a combination thereof. In some embodiments, the noncombustible material is selected from the group consisting of a metal, glass, silica, clay, or a combination thereof.

In some embodiments, the polymeric wall is in a shape selected from the group consisting of a cube, a cuboid, a sphere, a spheroid, a cylinder, a capsule shape and a rectangular prism. In some embodiments, dosage form is in a shape selected from the group consisting of a cube, a cuboid, a sphere, a spheroid, a cylinder, a capsule shape and a rectangular prism.

In some embodiments, the polymeric wall has a thickness in the range of 1 mm to 2 mm. In some embodiments, the polymeric wall has a thickness in the range of 1.5 mm to 2 mm. In some embodiments, the polymeric wall has a thickness in the range of 1 mm to 1.5 mm. In some embodiments, the polymeric wall has a thickness within a specific range, such that the dosage form is resistant to breaking upon application of external force by a user's fingers. In some embodiments, the polymeric wall has a thickness within a specific range, such that the dosage form is resistant to breaking upon application of external force of 250 N.

In some embodiments, the active material is present in an amount in the range of 5% to 70% w/w based on the weight of the dosage form. In some embodiments, the active material is present in an amount in the range of 5% to 60% w/w based on the weight of the dosage form. In some embodiments, the active material is present in an amount in the range of 7% to 50% w/w based on the weight of the dosage form. In some embodiments, the active material is present in an amount in the range of 8% to 40% w/w based on the weight of the dosage form. In some embodiments, the active material is present in an amount in the range of 10% to 30% w/w based on the weight of the dosage form.

In some embodiments, there is provided a dosage form for smoking, vaporization and/or inhalation, the dosage form comprising an active material comprising at least one cannabis ingredient mixed with a gellable polyol, wherein said dosage form comprises no more than 5% water.

In some embodiments, the dosage form comprises no more than 3% water. In some embodiments, the dosage form comprises no more than 1% water.

In some embodiments, there is provided a method for preparing a temperature dependent dosage form for smoking, vaporization and/or inhalation, the method comprising: injecting a measured amount of an active material into a gel comprising a gellable polysaccharide, wherein said active material includes an oil.

In some embodiments, there is provided a method for preparing a temperature dependent dosage form for smoking, vaporization and/or inhalation, the method comprising: (a) injecting a measured amount of an active material into a gel comprising a gellable polysaccharide and water, wherein said active material includes an oil; and (b) drying said gel, thereby forming a polymeric wall encapsulating said active material, wherein the drying includes removing at least 80% of the water.

In some embodiments, the drying includes removing at least 90% of the water. In some embodiments, the drying includes removing at least 80% of the water.

In some embodiments, the oil includes a cannabis ingredient. In some embodiments, the oil includes raw cannabis, cannabis extract and/or cannabis oil. In some embodiments, the oil includes cannabis. In some embodiments, the oil includes cannabis extract. In some embodiments, the oil includes cannabis oil. In some embodiments, the oil is cannabis oil. In some embodiments, the oil includes at least one terpene compound. In some embodiments, the oil is provided in the form of a mixture with at least one terpene compound. In some embodiments, the active material includes a mixture of an oil and at least one terpene compound. In some embodiments, the active material includes a mixture of cannabis oil and at least one terpene compound.

In some embodiments, the method further includes a step of inserting a solid core into said gel.

In some embodiments, the method further includes a step of adding a second polyol to the gel.

In some embodiments, the gel includes a gelling agent. In some embodiments, the gelling agent includes a gettable polyol. In some embodiments, the gelling agent includes a polysaccharide, a heteropolysaccharide, a polycarbohydrate, agarose, agar, agar-agar, cellulose, hydroxypropyl-cellulose, methylcellulose, hydroxypropylmethyl-cellulose, gelrite, phytagel, xanthan, xylinan, gellan, curdlan, pullulan, dextran, scleroglucan, schizophyllan or a combination thereof. In some embodiments, the gelling agent consists of a polysaccharide, a heteropolysaccharide, a polycarbohydrate, agarose, agar, agar-agar, cellulose, hydroxypropyl-cellulose, methylcellulose, hydroxypropylmethyl-cellulose, gelrite, phytagel, xanthan, xylinan, gellan, curdlan, pullulan, dextran, scleroglucan, schizophyllan, or a combination thereof.

In some embodiments, the method further includes a step of immersing in water a material selected from the group consisting of a gelling agent, a polysaccharide, a heteropolysaccharide, a polycarbohydrate, agarose, agar, agar-agar, cellulose, hydroxypropyl-cellulose, methylcellulose, hydroxypropylmethyl-cellulose, gelrite, phytagel, xanthan, xylinan, gellan, curdlan, pullulan, dextran, scleroglucan, schizophyllan, or a combination thereof, thereby forming the gel.

In some embodiments, the gel has a stiffness above a specific value when dry. In some embodiments, the gel has a stiffness above a specific value when dry, such that the dry gel is resistant to breaking upon application of external force by a person's fingers. In some embodiments, the gel has a stiffness above a specific value when dry, such that the dry gel is resistant to breaking upon application of external force of 250 N.

In some embodiments, the method further includes a step of shaping the gel in a shape selected from the group consisting of a cube, a cuboid, a sphere, a spheroid and a rectangular prism.

In some embodiments, there is provided a use of the dosage form described herein for smoking and/or inhalation.

In some embodiments, there is provided a use of the dosage form described herein for vaporization.

In some embodiments, there is provided a use of a dosage form comprising a polymeric wall encapsulating an active material, for smoking and/or inhalation.

In some embodiments, there is provided a use of a dosage form comprising a polymeric wall encapsulating an active material, for vaporization.

In some embodiments, there is provided a temperature dependent release dosage form for smoking and/or inhalation formed by injecting a measured amount of an active material into a gel comprising a gettable polysaccharide and water, wherein said active material includes an oil; and drying said gel, thereby forming a polymeric wall encapsulating said active material, wherein drying includes removing at least 60% of the water.

In some embodiments, drying includes removing at least 70% of the water. In some embodiments, drying includes removing at least 80% of the water. In some embodiments, drying includes removing at least 90% of the water. In some embodiments, drying includes removing at least 95% of the water. In some embodiments, drying includes removing at least 99% of the water.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIGS. 1A-C show a cross section of a temperature dependent release dosage form, according to some embodiments;

FIG. 2 shows a cross section of a temperature dependent release dosage form, according to some embodiments;

DETAILED DESCRIPTION

Figure 5:
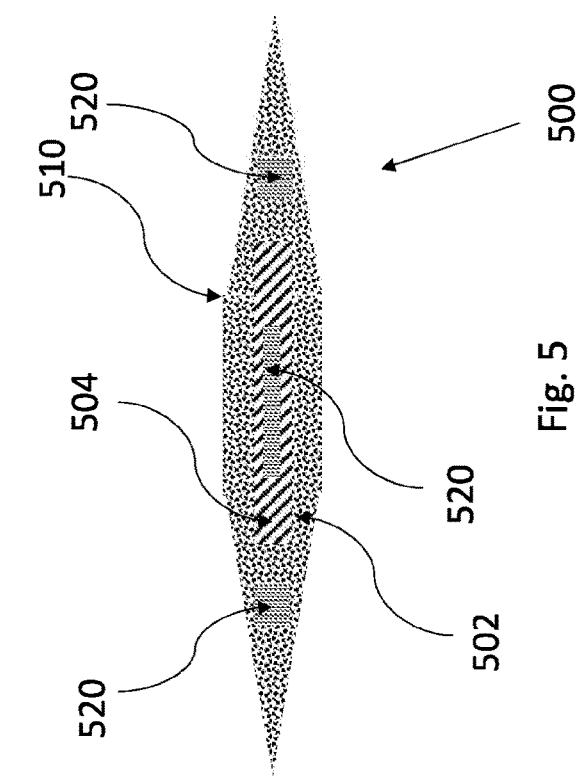
FIG. 5 shows a cross section of a temperature dependent release dosage form, according to some embodiments.

The following description relates to one or more non-limiting examples of embodiments of the invention. The invention is not limited by the described embodiments or drawings, and may be practiced in various manners or configurations or variations. The terminology used herein should not be understood as limiting unless otherwise specified.

The non-limiting section headings used herein are intended for convenience only and should not be construed as limiting the scope of the invention.

The "term temperature dependent release" is intended to mean that the release of an active material from a composition or a dosage form can be modified in connection with the surrounding temperature. Specifically, the term means that the rate of release is increased by raising the temperature of the surrounding media or environment. For example, a dosage form comprising an active material in its core, surrounded by a wall, will release the active material, when it passes through the wall, which in its turn is sensitive to conditions such as, but not limited to, deformations, consumption, disintegration, decomposition and the like, when exposed to temperature elevation. The "term temperature dependent release" is also intended to include cases in which the wall of the dosage form is at least partially burned, vaporized or combusted, such that the active material can pass therethrough.

The term "polyol", as used herein, is amply known in the art and describes a hydrocarbon compound comprising more than one hydroxyl group. Thus, non-limiting polyols include such materials as a carbohydrate, a polysaccharide, glycerin, a heteropolysaccharide, a polycarbohydrate, agarose, agar, agar-agar, cellulose, hydroxypropyl-cellulose, methylcellulose, hydroxypropylmethyl-cellulose, gelrite, phytagel, xanthan, xylinan, gellan, curdlan, pullulan, dextran, scleroglucan, schizophyllan, alginic acid, sodium alginate and the like. The term "polyol" also includes polyol salts, such as sodium alginate and esters, such as ethyl cellulose.

As used herein, the term "polysaccharide" is understood to encompass long linear or branched carbohydrate molecules of repeated monomer units joined together by glycosidic bonds, and complex carbohydrates composed of a chain of monosaccharides joined together by glycosidic bonds. More specifically, the term refers to polymers comprising a backbone comprising at least 90% of monosaccharide repeating units and/or derivatized monosaccharide repeating units. Non-limiting examples include starches, modified starches, amylopectin, modified amylopectin, amylose, modified amylose, chitosan, chitin, guar gum, modified guar gum, locust bean gum, tara gum, konjac gum, konjac flour, fenugreek gum, mesquite gum, aloe mannans, cellulose, modified cellulose, oxidized polysaccharides, sulfated polysaccharides, cationic polysaccharides, pectin, arabic gum, karaya gum, xanthan, kappa, iota or lambda carrageenans, agar-agar and alginates.

The term "gel" as used herein, refers in a broad sense to a semi-solid system having a solid phase dispersed in a liquid phase, wherein the solid phase is the continuous phase and the liquid is the discontinuous phase. The particles forming the solid phase are no longer independent kinetic units, but are spatially fixed due to a particular structural arrangement, such as by forming secondary connections, e.g. van der Waal's interactions or hydrogen bonds. It is intended to represent the physical, gelatinous characteristic of the composition.

The terms "gel forming agent" and "gelling agent" as used herein are interchangeable and refer to various gelling and viscosity agents, solution binders, thickeners, emulsifiers. In some embodiments, the thickening agent is employed in an amount effective to form a semi-solid that is substantially translucent and is sufficiently viscous. Gel forming agents include agents, which form a semi-crystalline structure by reaction with another material or by lowering of the temperature thereof while dissolved or colloidally suspended in a liquid medium. Gels can be either formed with a single or with a mixture of gel forming agents.

The term "gellable" as used herein, refers to a compound, which is capable of forming a gel upon contact with water. Typically, gel forming agents are gellable. In addition, many polyols, including, but not limited to, carbohydrates, such as polysaccharides, are gellable.

As used herein, the term "about" refers to a range of values +10% of a specified value. For example, the phrase "about 10" includes ±10% of 10, or from 9 to 11.

The term "hysteresis" refers to a retardation of an effect when the forces acting upon a body are changed. For example, hysteresis include softening or decomposition of a material under heat.

The term "stiffness" as used herein denote a characteristic of an element describing the resistance of the element against deformation or deflection, upon application of external force. That is, a material or element having a higher stiffness may have a smaller deflection and compliance than a material or element having a smaller stiffness when exposed to the same force trying to deflect or move the element. In general, high stiffness is important for improving durability of various products. Without wishing to be bound by any theory or mechanism, when a cannabis user commences in introducing a dosage form for smoking, inhalation and/or vaporization into an appropriate device, he/she should handle the dosage form in a manner such that it would keep its integrity. A more stiff dosage form would obviate this obstacle and allow the user a lesser degree of caution and mindfulness.

The term "not substantially dissolve in water" at a given temperature means that the dissolution rate of a solid at a given temperature is below 0.1 gram per 100 mL of water in 1 hour. Preferably, the rate is below 0.01 gram per 100 mL of water in 1 hour.

In some embodiments, the polymeric wall is in a shape selected from the group consisting of a cube, a cuboid, a sphere, a spheroid, a cylinder, a capsule shape and a rectangular prism. Such shapes are intended to include approximated shapes. For example, a ball having a recess(es) and/or a bump(s) will be an approximated sphere, and thus will be included under the definition of sphere. An elongated object, such as a toothpick shaped object, will be included under the definition of spheroid or a spheroid.

The terms "non-stick" and "non-sticky" as used herein, are interchangeable and signifies a surface that resists adherence of substances. In particular, when referring to dosage form intended to be handled by users, the term "non-stick" means that the dosage form, or in particular, its outer shell, does not stick to the user's fingers, thus making it easily handled.

The term "combustion promoter" refers to a chemical compound, which promotes partial or full combustion or burning. Such materials include combustible materials, such as aromatic or aliphatic hydrocarbons, and the like.

The term "combustible" means any combustible material. Specifically, combustible materials include materials or mixtures of materials suitable for use in a smoking composition. Materials or mixtures of materials suitable for use in a smoking composition include materials or mixtures that will burn under standard burning temperatures typical to smoking devices (e.g. the burning temperatures of a cigarette, a pipe, and the like), with respect to the ease of ignition of the combustible materials in such devices. Non-limiting examples of combustible materials include polyol, such as polysaccharides, and the like.

As used herein, the term "vaporization" will be interpreted in its conventional sense as defining the phase transition from the liquid state to the gaseous (vapour) state by transformation of molecules into a gas phase by evaporation, sublimation, boiling, and the like.

The term "weight" refers to any relatively heavy load, mass, or object. Specifically, as used herein, weight refers to an object, which is a part of an assembly, such as a dosage form, and is used in order to have a physical effect on the dosage form, by increasing its total mass, without effecting its chemical properties. As a result, a typical weight is chemically inert. For example, in cases where the dosage form is to be subjected to elevated temperature and/or combustion, the weight should be able to withstand high temperatures and should also be noncombustible. Such materials may include, for example, a metal, glass, silica, clay, and the like. Also, when used in dosage forms, the weight should be heavy relative to the total dosage form weight, such that it constitutes 25-99% of its total weight.

The term "cannabis ingredient" is used herein to refer to all physiologically active substances derived from the cannabis family of plants and synthetic cannabis analogues and derivatives, precursors, metabolites, etc., or related substances having cannabis-like physiological effects. Cannabis ingredients include, but are not limited to, cannabinoid acids and cannabinoids, such as THC, CBD and CBG.

The terms "cannabis" and "raw cannabis" as used herein are interchangeable and refer to cannabis indica and/or cannabis sativia cultivars used throughout history for their therapeutic and medical properties. These cultivars are generally higher in THC, as well as many other cannabinoids. Generally, the resinous exudates are the most valued part of the plant because they contain the highest concentration of THC. The term cannabis also encompasses the use of the flowering tops or buds, fruit, seeds, leaves, stems, and bark of the hemp plant.

The term "terpene" and "terpene compound" as used herein are interchangeable and are used in their broader sense. They include both terpene hydrocarbons, terpenoids and derivatives thereof, which may be considered as terpene hydrocarbons which have been modified by substitution or addition thereto, elements or groups containing elements such as oxygen, sulfur, nitrogen, halogens and so forth. The terms are further intended to mean, without limitations, mono-, di-, sesqui-, triterpenes and all related derivatives, as well as a mixture of these compounds. Generally, terpene compounds are in the form of an oil in room temperature.

The term "decarboxylation", as used herein, refers to an initiated process step, which is taken prior to the processing of the active material into a dosage form, wherein cannabis plant material has been treated such that the cannabinoid acids present in the untreated cannabis plant material have been transformed into the corresponding free cannabinoids. Decarboxylation is usually carried out by heating the cannabis plant material. Typically, decarboxylated cannabinoids have significantly stronger therapeutic activity than the corresponding cannabinoid acids, thus the decarboxylation step is often required.

In some embodiments, the dosage forms and methods of the current disclosure enable the use of naturally obtained cannabis ingredients, contrary to other products known in the art, which require a preliminary decarboxylation step of the raw cannabis plant material.

The term "drying" means removal of at least a portion of the liquids, such as water, which are present in a product or a substance. For example, for a gel, which contains water, drying will include removing at least a portion of the water. Drying include heating, vacuum drying, sublimation, evaporation, such as evaporation by exposure to environmental air, and the like.

As used herein, the term "measured amount", when referring to active material, relates to an amount of the material, which is quantitative or semi-quantitative measured prior to incorporation in a dosage form, a pharmaceutical composition, and the like. When specifically referring to cannabis, cannabis extract and/or cannabis oil, the measurement may preferably include a volumetric measurement of weight (or mass) measurement. Due to the cannabis oil's high viscosity, such measurement tends to be highly inaccurate when performed by the users. Therefore, in the current situation, when cannabis users are provided with cannabis, they do not consume a measured amount of the active material, rather approximated amounts, which may be highly various. In contrast, the present method and dosage form, in some embodiments, enable the delivery of a measured amount of an active material to the user.

Reference is made to FIG. 1A, which schematically shows a cross section of a temperature dependent release dosage form 100 including a polymeric wall 110 and a core 102. Dosage form 100 includes an approximately spherical three dimensional shape. Dosage form 100 is configured to be used for smoking, vaporization, and the like. For example, dosage form 100 may be inserted inside a cigarette or a corresponding rolling paper for smoking, and be smoked. Alternatively, dosage form 100 may replace or be used together with a designated smoking material in a water pipe, bong, hookah, smoking bottle, and the like.

Core 102 includes an active material 104. In some embodiments, core 102 is surrounded by polymeric wall 110.

Active material 104 includes cannabis oil. Active material 104 is located inside core 102 of dosage form 100 and is surrounded by polymeric wall 110. The cannabis oil of active material 104 includes less than 10% decarboxylated moieties based on the total number of carboxylic moieties in active material 104. When dosage form 100 is used in a smoking device, active material 104 may vaporize upon heating given that the formed vapors can pass through polymeric wall 110, as explained below.

Polymeric wall 110 is configured to surround core 102 and active material 104. As can be seen in FIG. 1A, polymeric wall 110 constitutes the outermost layer of dosage form 100 and is non-sticky, thus allowing the user easy manipulation of dosage form 100 by hand.

Polymeric wall 110 is configured to prevent passage of active material 104 therethrough at temperatures lower than 50° C., and to allow its passage at temperatures higher than 80° C. Polymeric wall 110 is composed of agar including no more than about 10% water. Without wishing to be bound by any theory or mechanism of action, the feature of allowing passage of water through polymeric wall 110 only above certain temperatures is generally achieved by the composition of polymeric wall 110, which is temperature sensitive, thus promoting disintegration of polymeric wall 110 at elevated temperatures. Specifically, polymeric wall 110 does not melt or deform at temperatures lower than 50° C. This is since the agar composition constituting polymeric wall 110 does not melt or deform at temperatures lower than 50° C. In contrast, above 80° C. the agar composition constituting polymeric wall 110 may start to melt and/or deform. Therefore, polymeric wall 110 may melt or deform at temperatures higher than 80° C., thus allowing the passage of active material 104 above this temperature. This temperature range is specifically favorable for smoking, vaporization and/or inhalation purposes, which require elevated temperatures, while the dosage forms used for such purposes are typically stored at room temperature or below, without risk of disintegration due to high environment temperature. Furthermore, since agar including no more than about 10% water is combustible, polymeric wall 110 may be burned in a process of smoking, thus allowing the passage of active material 104 through polymeric wall 110 under combustion conditions.

Polymeric wall 110 is generally thick relative to the dimensions of dosage form 100. The thickness confers to polymeric wall 110 a high degree of stiffness. Specifically, polymeric wall 110 has stiffness, such that dosage form 100 is resistant to breaking upon application of external force of 250 N. These features are achieved by the amount and physical properties of the agar composition forming polymeric wall 110.

A high degree of stiffness and stability of dosage form 100, conferred from the stiffness of polymeric wall 110, is important for the easy handling and durability of dosage forms, which are intended for use by cannabis users, especially, when the use is by smoking, vaporization and/or inhalation.

As seen in FIG. 1A, polymeric wall 110 is approximately in the shape of a sphere, which may also ease the use of dosage form 100, which also receives a spherical shape.

Reference is made to FIG. 1B, which schematically shows a cross section of temperature dependent release dosage form 100 including polymeric wall 110 and core 102, which includes active material 104. In FIG. 1B, dosage form 100 is exposed to elevated temperatures.

In FIG. 1B, polymeric wall 110, which constitutes the outermost layer of dosage form 100, is exposed to elevated temperatures. Therefore, polymeric wall 110 is partially decomposed. Specifically, a bottom end 112 of polymeric wall 110 is exposed to temperatures higher than 80° C., which results in its partial decomposition and formation of a slit 114 in polymeric wall 110. As described above, the agar composition constituting polymeric wall 110 may start to melt, burn and/or deform upon exposure to temperatures higher than 80° C. and, as a result, form a slit(s), such as slit 114.

Reference is made to FIG. 1C, which schematically shows a cross section of temperature dependent release dosage form 100 including polymeric wall 110 and core 102, which includes active material 104. In FIG. 1B, dosage form 100 is exposed to elevated temperatures, which results in dripping of active material 104 therefrom.

In FIG. 1C, polymeric wall 110, which constitutes the outermost layer of dosage form 100, is exposed to elevated temperatures. Therefore, polymeric wall 110 is partially decomposed. Specifically, a bottom end 112 of polymeric wall 110 is exposed to temperatures higher than 80° C., which results in its partial decomposition and formation of a slit 114 in polymeric wall 110 as in FIG. 1B. As described above, the agar composition constituting polymeric wall 110 may start to melt, burn and/or deform upon exposure to temperatures higher than 80° C., and as a result, form a slit(s), such as slit 114.

As can be seen in FIG. 1C, active material 104 is dripping through slit 114, by gravitation. As a result, polymeric wall 110 allows passage of active material 104 therethrough at temperatures higher than 80° C. At these temperatures, the cannabis oil of active material 104 evaporates, as illustrated by arrows 106, thereby allowing dosage form 100 to be used for smoking and/or inhalation by a user, with a designated smoking device, such as a water pipe, bong, hookah, smoking bottle, and the like.

Reference is made to FIG. 2, which schematically shows a cross section of a temperature dependent release dosage form 200, including a polymeric wall 210 and a core 202. Dosage form 200 includes an approximately spherical three dimensional shape. Dosage form 200 is configured to be used for smoking, vaporization, and the like. For example, dosage form 200 may be inserted inside a cigarette or a corresponding rolling paper for smoking, and be smoked. Alternatively, dosage form 200 may replace or be used together with a designated smoking material in a water pipe, bong, hookah, smoking bottle, and the like.

Core 202 includes an active material 204. As presented in FIG. 2 core 202 has a larger volume than active material 204, such that a void 208 is formed in the space, which is not occupied by active material 204. Core 202 is surrounded by polymeric wall 210.

In some embodiments, temperature dependent release dosage form 200 is formed by injecting a measured amount of active material 204 into a polymeric gel; and drying the gel, thereby forming polymeric wall 210.

Active material 204 includes cannabis oil. Active material 204 is located inside core 202 of dosage form 200 but, since its volume is smaller than the volume of core 202, a void 208 is formed in the remaining space. As dosage form 200 is formed by injecting active material 204 into a polymeric gel, which is to be dried, the amount of active material 204 may be relatively accurately measured, for example, using a syringe. As a result, different versions of dosage forms may be formed with various amounts of active material, wherein the amounts are measured.

Polymeric wall 210 is configured to surround core 202 and active material 204. As can be seen in FIG. 2, polymeric wall 210 constitutes the outermost layer of dosage form 200. As a result of its drying, it is non-sticky, thus allowing the user easy manipulation of dosage form 200 by hand.

Polymeric wall 210 is configured to prevent passage of active material 204 therethrough at temperatures lower than 45° C., and to allow its passage at temperatures higher than 85° C. Polymeric wall 210 is composed of agar, which constituted the gel used for its preparation, where the agar of polymeric wall 210 includes no more than about 8% water, due to the drying process. Without wishing to be bound by any theory or mechanism of action, the feature of allowing passage of water through polymeric wall 210 only above certain temperatures is generally achieved by the composition of polymeric wall 210, which is temperature sensitive, thus promoting disintegration of polymeric wall 210 at elevated temperatures. Specifically, polymeric wall 210 does not melt or deform at temperatures lower than 45° C. This is since the agar composition constituting polymeric wall 210 does not melt or deform at temperatures lower than 45° C. In contrast, above 85° C. the agar composition constituting polymeric wall 210 may start to melt and/or deform. Therefore, polymeric wall 210 may melt or deform at temperatures higher than 85° C., thus allowing the passage of active material 204 above this temperature. Furthermore, since agar including no more than about 8% water is combustible, polymeric wall 210 may be burned in a process of smoking, thus allowing the passage of active material 204 through polymeric wall 210 under combustion conditions.

Figure 3:
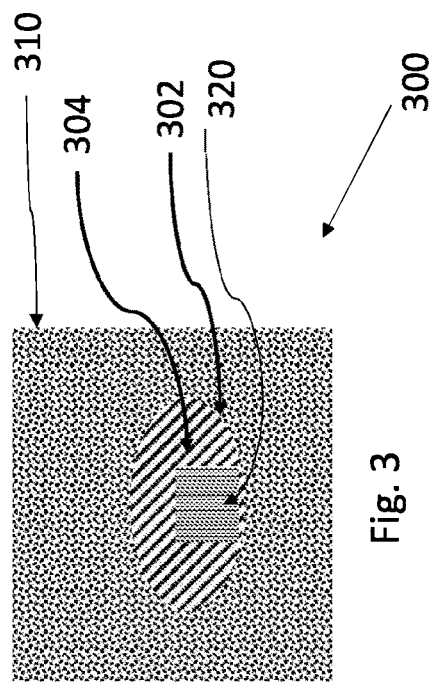
FIG. 3 shows a cross section of a temperature dependent release dosage form, according to some embodiments.

Reference is made to FIG. 3, which schematically shows a cross section of a temperature dependent release dosage form 300, including a polymeric wall 310 and a core 302. Dosage form 300 includes an approximately cubical three dimensional shape. Dosage form 300 is configured to be used for smoking, vaporization, and the like. For example, dosage form 300 may be inserted inside a cigarette or a corresponding rolling paper for smoking, and be smoked. Alternatively, dosage form 300 may replace or be used together with a designated smoking material in a water pipe, bong, hookah, smoking bottle, and the like.

Core 302 includes an active material 304 and a weight 320 surrounded by polymeric wall 310.

Active material 304 includes cannabis extract. Active material 304 is located inside core 302 of dosage form 300 and is surrounded by polymeric wall 310. The cannabis extract of active material 304 includes less than 5% decarboxylated moieties based on the total number of carboxylic moieties in active material 304.

Weight 320 is located inside core 302 of dosage form 300 and is surrounded by polymeric wall 310. Weight 320 consists of a noncombustible material, such as metal, glass, silica, clay, and the like. The noncombustible material is also stable towards heat and nonvolatile, such that, upon exposure of dosage form 300 to external heat, it may pass through polymeric wall 310, but it does not evaporate. Weight 320 is configured to provide dosage form 300 with an additional weight. This may ease the use of dosage form 300 and its incorporation in a smoking/inhalation device.

Polymeric wall 310 is configured to surround core 302, weight 320 and active material 304.

As seen in FIG. 3 polymeric wall 310 is approximately in the shape of a cube, which may also ease the use of dosage form 300, which also receives a cubical shape.

Figure 4:
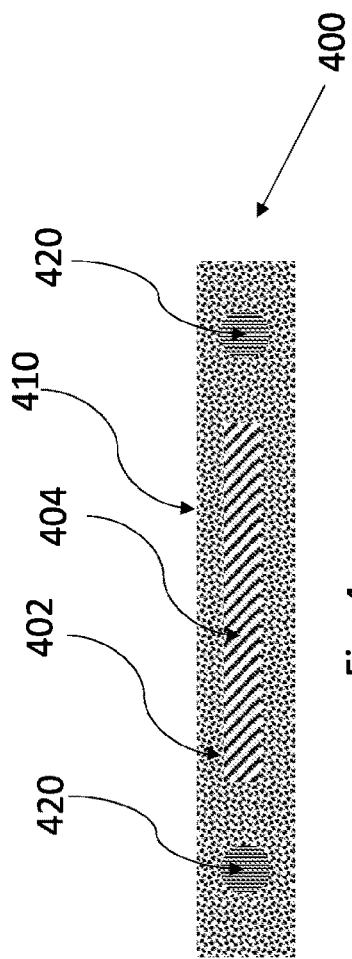
FIG. 4 shows a cross section of a temperature dependent release dosage form, according to some embodiments.

Reference is made to FIG. 4, which schematically shows a cross section of a temperature dependent release dosage form 400 including a polymeric wall 410, a core 402 and weights 420. Dosage form 400 includes an approximately rectangular three dimensional shape. Dosage form 400 is configured to be used for smoking, vaporization, and the like.

Core 402 includes an active material 404 surrounded by polymeric wall 410.

Active material 404 includes raw cannabis. Active material 404 is located inside core 402 of dosage form 400 and is surrounded by polymeric wall 410. The raw cannabis of active material 404 includes less than 7.5% decarboxylated moieties based on the total number of carboxylic moieties in active material 404.

Weights 420 are located inside polymeric wall 410 of dosage form 400. They are surrounded by polymeric wall 410. Weights 420 consist of a noncombustible material, such as metal, glass, silica, clay, and the like. The noncombustible material is also stable towards heat and nonvolatile, such that upon exposure of dosage form 400 to external heat, weights 420 may physically pass through polymeric wall 410, but they do not evaporate. Weights 420 are configured to provide dosage form 400 with an additional mass. This may ease the use of dosage form 400 and its incorporation in a smoking/inhalation device.

Polymeric wall 410 is configured to contain core 402, weights 420 and active material 404.

As seen in FIG. 4 polymeric wall 410 is approximately in the shape of a rectangle, which may also ease the use of dosage form 400, which also receives a similar shape.

Reference is made to FIG. 5, which schematically shows a cross section of a temperature dependent release dosage form 500 including a polymeric wall 510, a core 502 and weights 520. Dosage form 500 includes an elongated three dimensional shape, similar to a toothpick. Dosage form 500 is configured to be used for smoking, vaporization, and the like.

Core 502 includes an active material 504 surrounded by polymeric wall 510.

Active material 504 includes cannabis oil. Active material 504 is located inside core 502 of dosage form 500 is surrounded by polymeric wall 510. The cannabis oil of active material 504 includes less than 2.5% decarboxylated moieties based on the total number of carboxylic moieties in active material 504.

Weights 520 are located inside polymeric wall 510 and inside core 502 of dosage form 500. They are surrounded by polymeric wall 510. Weights 520 consist of a noncombustible material, such as metal, glass, silica, clay, and the like. The noncombustible material is also stable towards heat and nonvolatile, such that upon exposure of dosage form 500 to external heat, weights 520 may physically pass through polymeric wall 510, but they do not evaporate. Weights 520 are configured to provide dosage form 500 with an additional mass, which may ease the use of dosage form 500 and its incorporation in a smoking/inhalation device.

Polymeric wall 510 is configured to contain core 502, weights 520 and active material 504.

As seen in FIG. 5 polymeric wall 510 is approximately in the shape of a toothpick, which may also ease the use of dosage form 500, which also receives a similar shape.

Figure 6C:
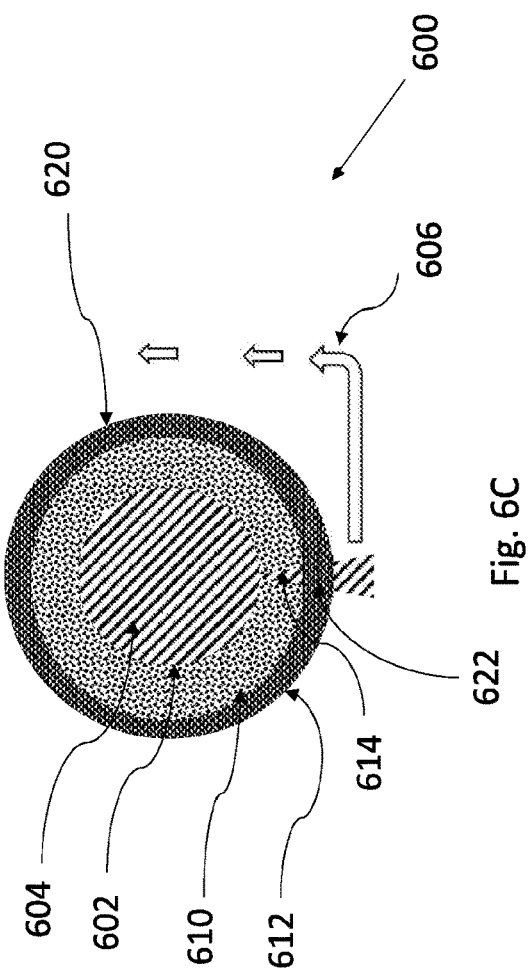
FIG. 6C shows a cross section of a temperature dependent release dosage form, according to some embodiments.
Figure 6A:
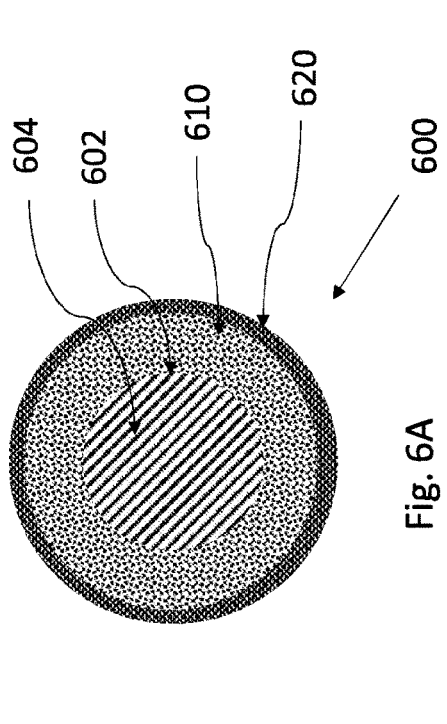
FIG. 6A shows a cross section of a temperature dependent release dosage form, according to some embodiments.

Reference is made to FIG. 6A, which schematically shows a cross section of a temperature dependent release dosage form 600 including a polymeric wall 610, an external weight 620 and a core 602. Dosage form 600 includes an approximately spherical three dimensional shape. Dosage form 600 is configured to be used for smoking, vaporization, and the like. For example, dosage form 600 may be inserted inside a cigarette or a corresponding rolling paper for smoking, and be smoked. Alternatively, dosage form 600 may replace or be used together with a designated smoking material in a water pipe, bong, hookah, smoking bottle, and the like.

Core 602 includes an active material 604. In some embodiments, core 602 is surrounded by polymeric wall 610.

Active material 604 includes cannabis oil. Active material 604 is located inside core 602 of dosage form 600 and is surrounded by polymeric wall 610. The cannabis oil of active material 604 includes less than 5% decarboxylated moieties based on the total number of carboxylic moieties in active material 604. When dosage form 600 is used in a smoking device, active material 604 may vaporize upon heating given that the formed vapors can pass through polymeric wall 610, as explained below.

Polymeric wall 610 is configured to surround core 602 and active material 604 and is surrounded by external weight 620. Polymeric wall 610 is configured to prevent passage of active material 604 therethrough at temperatures lower than 50° C., and to allow its passage at temperatures higher than 80° C. Polymeric wall 610 is composed of agar including no more than about 10% water. Without wishing to be bound by any theory or mechanism of action, the feature of allowing passage of water through polymeric wall 610 only above certain temperatures is generally achieved by the composition of polymeric wall 610, which is temperature sensitive, thus promoting disintegration of polymeric wall 610 at elevated temperatures. Specifically, polymeric wall 610 does not melt or deform at temperatures lower than 50° C. This is since the agar composition constituting polymeric wall 610 does not melt or deform at temperatures lower than 50° C. In contrast, above 80° C., the agar composition constituting polymeric wall 610 may start to melt and/or deform. Therefore, polymeric wall 610 may melt or deform at temperatures higher than 80° C., thus allowing the passage of active material 604 above this temperature. This temperature range is specifically favorable for smoking, vaporization and/or inhalation purposes, which require elevated temperatures, while the dosage forms used for such purposes are typically stored in room temperature or below, without risk of disintegration due to high environment temperature. Furthermore, since agar including no more than about 10% water is combustible, polymeric wall 610 may be burned in a process of smoking, thus allowing the passage of active material 604 through polymeric wall 110 under combustion conditions. As explained below, active material 604 may also pass through external weight 620.

External weight 620 surrounds core 602 and polymeric wall 610 of dosage form 600. As can be seen in FIG. 6A, it constitutes the outermost layer of dosage form 600. External weight 620 consists of a noncombustible material, such as metal, glass, silica, clay, and the like. The noncombustible material is also stable towards heat and nonvolatile, such that upon exposure of dosage form 600 to external heat, it is exposed to temperature elevation, but it does not evaporate. External weight 620 is configured to provide dosage form 600 with an additional weight. This may ease the use of dosage form 600 and its incorporation in a smoking/inhalation device.

External weight 620 is perforated. As a result, upon decomposition or deformation of polymeric wall 610 and passage of active material 604 therethrough, active material 604 may also pass through external weight 620, and depart dosage form 600.

As seen in FIG. 6A, polymeric wall 610 is approximately in the shape of a sphere, which may also ease the use of dosage form 600, which also receives a spherical shape.

Figure 6B:
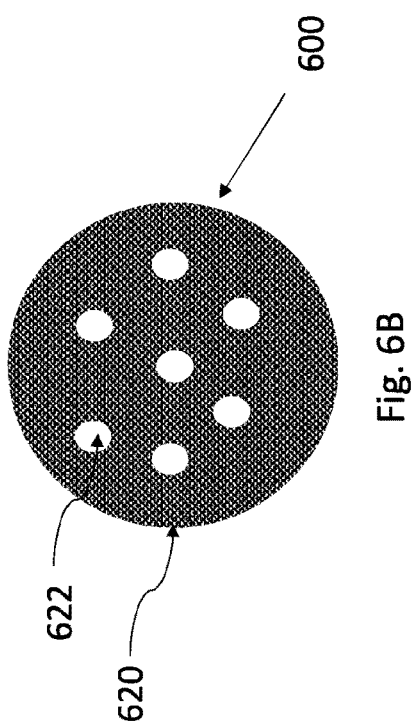
FIG. 6B shows a side view of an external weight of a temperature dependent release dosage form, according to some embodiments.

Reference is made to FIG. 6B, which schematically shows a side view of external weight 620 of temperature dependent release dosage form 600. As seen in the figure, weight 620 is perforated. Specifically, weight 620 includes holes 622. Holes 622 allow passage of fluid materials therethrough.

Reference is made to FIG. 6C, which schematically shows a cross section of temperature dependent release dosage form 600 including polymeric wall 610, external weight 620 and core 602, which includes active material 604. In FIG. 1C, dosage form 600 is exposed to elevated temperatures, which results in dripping of active material 604 therefrom.

In FIG. 6C, polymeric wall 610 is exposed to elevated temperatures. As a result, polymeric wall 610 is partially decomposed. Specifically, a bottom end 612 of polymeric wall 610 is exposed to temperatures higher than 80° C., which result in its partial decomposition and formation of a slit 614 in polymeric wall 610. As described above, the agar composition constituting polymeric wall 610 may start to melt, burn and/or deform upon exposure to temperatures higher than 80° C., and as a result, form a slit(s), such as slit 614. Nevertheless, since external weight 620, which constitutes the outermost layer of dosage form 600, is also stable towards heat, it is not burned or evaporated.

As can be seen in FIG. 6C, active material 604 is dripping through slit 614, by gravitation. Active material 604 is dripping through holes 622 of external weight 620. As a result, polymeric wall 610 and external weight 620 allow passage of active material 604 therethrough at temperatures higher than 80° C. At these temperatures, the cannabis oil of active material 604 evaporates, as illustrated by arrows 606, thereby allowing dosage form 600 to be used for smoking and/or inhalation by a user, with a designated smoking device, such as a water pipe, bong, hookah, smoking bottle, and the like.

Figure 7:
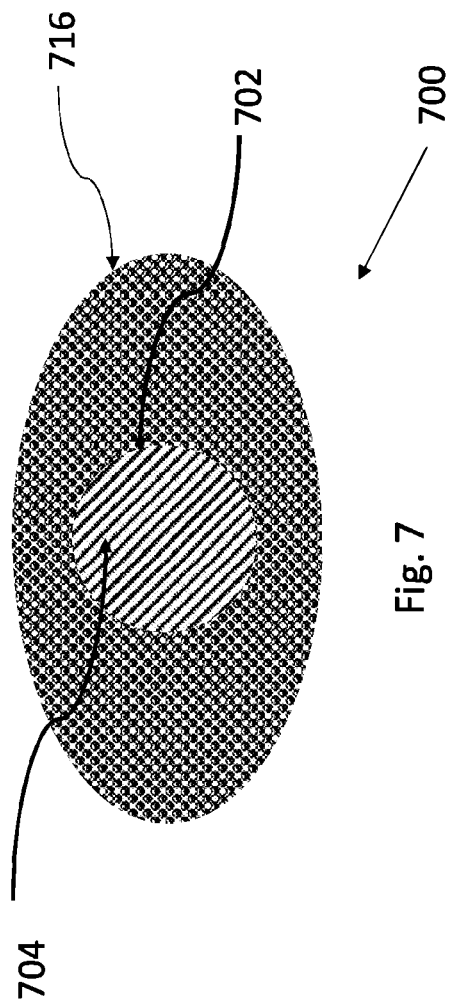
FIG. 7 shows a cross section of a temperature dependent release dosage form, according to some embodiments.

Reference is made to FIG. 7, which schematically shows a cross section of a temperature dependent release dosage form 700 including a wall 716 and a core 702. Dosage form 700 includes an approximately ellipsoidal three dimensional shape. Dosage form 700 is configured to be used for smoking, vaporization, and the like. For example, dosage form 700 may be inserted inside a cigarette or a corresponding rolling paper for smoking, and be smoked. Alternatively, dosage form 700 may replace or be used together with a designated smoking material in a water pipe, bong, hookah, smoking bottle, and the like.

Core 702 includes an active material 704 surrounded by wall 716.

Active material 704 includes cannabis extract. Active material 704 is located inside core 702 of dosage form 700 and is surrounded by wall 716. The cannabis extract of active material 704 includes less than 5% decarboxylated moieties based on the total number of carboxylic moieties in active material 704.

Wall 716 is configured to surround core 102 and active material 704. As can be seen in FIG. 1A, wall 716 constitutes the outermost layer of dosage form 700. It is non-sticky, thus allowing the user easy manipulation of dosage form 700 by hand. Wall 716 is configured to prevent passage of active material 704 therethrough at temperatures lower than 50° C., and to allow its passage at temperatures higher than 80° C. Wall 716 is composed of a mixture of agar and glycerin including no more than about 5% water. Without wishing to be bound by any theory or mechanism of action, the feature of allowing passage of water through wall 716 only above certain temperatures is generally achieved by the composition of wall 716, which is temperature sensitive, thus promoting disintegration of wall 716 at elevated temperatures. Specifically, polymeric wall 716 does not melt or deform at temperatures lower than 50° C. This is since the mixture comprising agar and glycerin, which constitutes wall 716 does not melt or deform at temperatures lower than 50° C. In contrast, above 80° C. the agar/glycerin mixture constituting wall 716 may start to melt and/or deform. Therefore, wall 716 may melt or deform at temperatures higher than 80° C., thus allowing the passage of active material 704 above this temperature. This temperature range is specifically favorable for smoking, vaporization and/or inhalation purposes, which require elevated temperatures, while the dosage forms used for such purposes are typically stored in room temperature or below, without risk of disintegration due to high environment temperature. Furthermore, since a mixture of agar and glycerin including no more than about 5% water is combustible, polymeric wall 716 may be burned in a process of smoking, thus allowing the passage of active material 704 through wall 716 under combustion conditions.

Wall 716 is generally thick relative to the dimensions of dosage form 700. The thickness confers to wall 716 a high degree of stiffness. These features are achieved by the amount and physical properties of the agar composition forming wall 716.

A high degree of stiffness and stability of dosage form 100, conferred from the stiffness of wall 716, is important for the easy handling and durability of dosage forms, which are intended for use by cannabis users, especially when the use is by smoking, vaporization and/or inhalation.

As seen in FIG. 7 polymeric wall 716 is approximately in the shape of an ellipsoid, which may also be of ease in the use of dosage form 700, which also receives an ellipsoidal shape.

Figure 8:
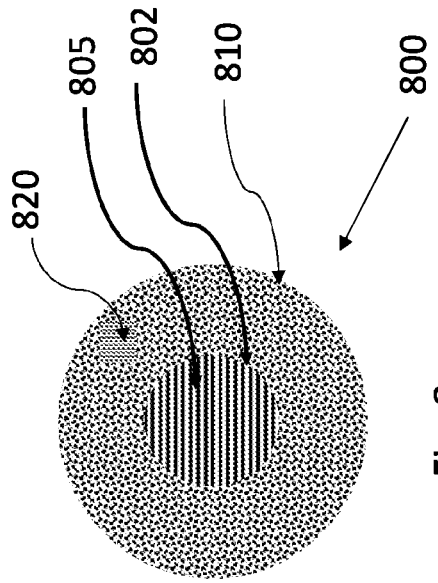
FIG. 8 shows a cross section of a temperature dependent release dosage form, according to some embodiments.

Reference is made to FIG. 8, which schematically shows a cross section of a temperature dependent release dosage form 800 including a polymeric wall 810 and a core 802. Dosage form 800 includes an approximately spherical three dimensional shape. Dosage form 800 is configured to be used for smoking, vaporization, and the like. For example, dosage form 800 may be inserted inside a cigarette or a corresponding rolling paper for smoking, and be smoked. Alternatively, dosage form 800 may replace or be used together with a designated smoking material in a water pipe, bong, hookah, smoking bottle, and the like.

Core 802 includes an active material 805 surrounded by polymeric wall 810.

Active material 805 includes a mixture of cannabis oil and agar. Active material 805 is located inside core 802 of dosage form 800 and is surrounded by polymeric wall 810. The cannabis oil of active material 805 includes less than 10% decarboxylated moieties based on the total number of carboxylic moieties in active material 805. When dosage form 800 is used in a smoking device, active material 805 may at least partially vaporize upon heating given that the formed vapors can pass through polymeric wall 810 as explained below.

Polymeric wall 810 is configured to surround core 802, weight 820 and active material 805.

Figure 9:
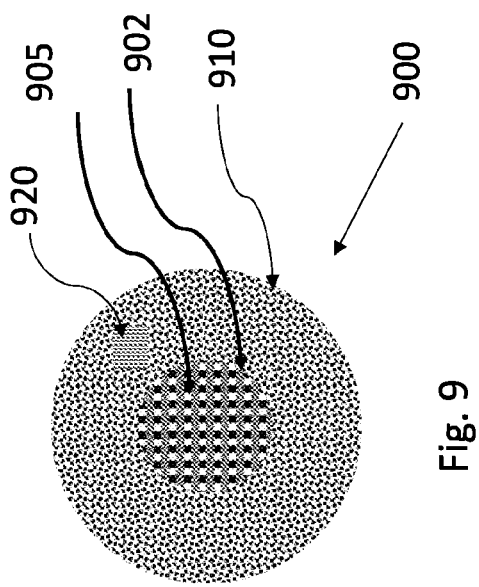
FIG. 9 shows a cross section of a temperature dependent release dosage form, according to some embodiments.

Reference is made to FIG. 9, which schematically shows a cross section of a temperature dependent release dosage form 900 including a polymeric wall 910 and a core 902. Dosage form 900 includes an approximately spherical three dimensional shape. Dosage form 900 is configured to be used for smoking, vaporization, and the like. For example, dosage form 900 may be inserted inside a cigarette or a corresponding rolling paper for smoking, and be smoked. Alternatively, dosage form 900 may replace or be used together with a designated smoking material in a water pipe, bong, hookah, smoking bottle, and the like.

Core 902 includes an active material 905 surrounded by polymeric wall 910.

Active material 905 includes a mixture of cannabis oil and a terpene mixture. Active material 905 is located inside core 902 of dosage form 900 and is surrounded by polymeric wall 910. The cannabis oil of active material 905 includes less than 10% decarboxylated moieties based on the total number of carboxylic moieties in active material 905. When dosage form 900 is used in a smoking device, active material 905 may at least partially vaporize upon heating given that the formed vapors can pass through polymeric wall 910 as explained below.

Polymeric wall 910 is configured to surround core 902, weight 920 and active material 905.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

The invention claimed is:

1. A method for preparing a temperature dependent release dosage form comprising 30% to 70% w/w of a liquid cannabis ingredient comprising cannabis extract, cannabis oil, THC, CBD and/or CBG; a combustible polymeric wall encapsulating the liquid cannabis ingredient, wherein the polymeric wall comprises agar, agar-agar, or agarose, and no more than about 5% w/w water, the method comprising:
   immersing agar, agar-agar, or agarose in water, thereby forming a gel mixture,
   injecting the liquid cannabis ingredient into the gel mixture;
   drying the liquid cannabis ingredient-injected gel mixture, thereby obtaining a dosage form comprising the liquid cannabis ingredient encapsulated in the combustible polymeric wall comprising agar, agar-agar, or agarose; and
   shaping the dosage form into a desired form,
   wherein said dosage from is a gelatinous, non-sticky dosage form suitable for smoking, and wherein disintegration of said dosage form is prevented by said combustible polymeric wall at temperatures lower than about 60° C. while at temperatures higher than 80° C., the disintegration is triggered.

2. The method of claim 1, wherein the polymeric wall comprises agar.

3. The method of claim 2, wherein the dosage form further comprises glycerin.

4. The method of claim 1, wherein the desired shape is an elongated shape.

5. The method of claim 4, wherein the elongated shape is a toothpick shape.

6. The method of claim 1, wherein the desired shape is selected from cube shape, cuboid shape, sphere shape, spheroid shape, cylinder shape, capsule shape and rectangular shape.

7. The method of claim 1, wherein the liquid cannabis ingredient is non-decarboxylated.

8. The method of claim 1, further comprising inserting the dosage form inside a cigarette, cigar, hand rolled cigarette, or a rolling paper for smoking.

9. The method of claim 1, wherein the dosage form is characterized by said combustible polymeric wall preventing disintegration of said dosage form at temperatures lower than about 70° C. while triggering the disintegration at temperatures higher than 120° C.

* * * * *